(12) United States Patent
Marquardt et al.

(10) Patent No.: US 12,124,615 B2
(45) Date of Patent: Oct. 22, 2024

(54) CONTROL SYSTEM FOR A PROCESS CONTROL

(71) Applicant: Drägerwerk AG & Co. KGaA, Lübeck (DE)

(72) Inventors: Klaus Marquardt, Lübeck (DE); Thomas Mond, Lübeck (DE); Hannes Molsen, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 575 days.

(21) Appl. No.: 17/369,570

(22) Filed: Jul. 7, 2021

(65) Prior Publication Data

US 2022/0013225 A1  Jan. 13, 2022

(30) Foreign Application Priority Data

Jul. 8, 2020 (DE) ...................... 10 2020 117 983.9

(51) Int. Cl.
*G06F 21/64* (2013.01)
*G06F 21/60* (2013.01)
*H04L 9/32* (2006.01)

(52) U.S. Cl.
CPC ............ *G06F 21/64* (2013.01); *H04L 9/3242* (2013.01); *H04L 9/3247* (2013.01); *G06F 21/602* (2013.01)

(58) Field of Classification Search
CPC ..... G06F 21/64; G06F 21/602; H04L 9/3242; H04L 9/3247; H04L 9/0643; H04L 2209/80; G16H 40/63
See application file for complete search history.

(56) References Cited

U.S. PATENT DOCUMENTS

| | | | |
|---|---|---|---|
| 6,502,192 B1 * | 12/2002 | Nguyen | .................. H04L 63/08 726/4 |
| 10,042,993 B2 | 8/2018 | Beigi | |
| 10,367,786 B2 * | 7/2019 | Gaitonde | ............ H04L 63/0218 |
| 2012/0173702 A1 * | 7/2012 | Szabo | ................... H04L 67/535 709/224 |
| 2020/0266989 A1 * | 8/2020 | Krcmaricic-Barackov | ................. H04L 9/30 |

FOREIGN PATENT DOCUMENTS

EP   2352971 B1   2/2015
EP   3101491 B1   4/2019

\* cited by examiner

*Primary Examiner* — Azizul Choudhury
(74) *Attorney, Agent, or Firm* — McGlew and Tuttle, P.C.

(57) ABSTRACT

A control system (100) for a device (105) for making possible a process control for a process carried out on the device, with a reception module (110) and with a processing module (120). The reception module is configured to receive process information (112). The process information pertains to currently carried out process steps (114) of the process. The processing module is configured to assign a sequence number (122) to the received process information and to generate a visible protocol signature (128) based on the sequence number, of the process information, of time information (124) and a secret system code (126) and to assign it to the process information, and to output the process information with the assigned visible protocol signature. The secret system code is stored n this case exclusively in an internal memory (125) of the control system.

20 Claims, 5 Drawing Sheets

CONTROL SYSTEM FOR A PROCESS CONTROL

CROSS REFERENCE TO RELATED APPLICATIONS

This application claims the benefit of priority under 35 U.S.C. § 119 of German Application 10 2020 117 983.9, filed Jul. 8, 2020, the entire contents of which are incorporated herein by reference.

TECHNICAL FIELD

The present invention pertains to a control system for a device for making possible a process control for a process carried out on the device. The present invention pertains, furthermore, to a medical device with a corresponding control system, to a process for making possible a process control for a process carried out on a device, and to a computer program with a program code for carrying out a corresponding process.

TECHNICAL BACKGROUND

It is known that process information on currently carried out process steps, e.g., log files of a device, can be encrypted. Such an encryption may be carried out symmetrically via a single protocol code for decryption or asymmetrically via a first public protocol code and a second private protocol code.

Furthermore, it is known that process information on currently carried out process steps, e.g., a log file, can be verified with a signature. Such a signature may be, for example, a check sum, which is unambiguously assigned to the process information, and which makes it retrospectively possible to check whether a change has occurred within the log files. Such a changed log file would lead, for example, to a different check sum, and it would be detected against this background in view to the stored check sum.

SUMMARY

An object of the present invention is to provide an improved control system, especially a control system that makes it possible to reliably detect a change within stored process information.

According to a first aspect of the present invention, a control system is proposed for a process carried out on the device, with a reception module and with a processing module for accomplishing this object.

The reception module is configured to receive process information, wherein the process information pertains to currently performed process steps of the process.

The processing module is configured to assign a sequence number to the received process information and to generate a visible protocol signature on the basis of the sequence number, of the process information, of time information and a secret system code of the control system and to assign this to the process information and to output the process information with the assigned visible protocol signature. The secret system code is stored exclusively in an internal memory of the control system.

It was found within the framework of the present invention that a manipulation of the process information must be prevented and/or detected especially reliably in some devices, e.g., medical devices. It was found for this that the corresponding secret system code, which shall prevent an unnoticed manipulation, must not either be outputted at the device nor must it be stored at a location outside the device. This is accomplished according to the present invention by the secret system code being stored exclusively in the internal memory. As a result, the visible protocol signature is generated via the secret system code such that no other device can change the process information and adapt the corresponding protocol signature such that this remains unnoticed.

It is advantageously ensured hereby that a data pair of process information and assigned visible protocol signature fit together only if the process information was not changed later, after the visible protocol signature was generated. Such a change would lead to a change of the protocol signature to be assigned via the secret system code, which cannot be determined without the knowledge of the secret system code.

Complete removal of process information, e.g., of a log file, likewise becomes demonstrable, because the time information and the sequence number are likewise contained in an encrypted form in the visible protocol signature. If the process information is missing at a defined time and/or if the sequence number differs from a selected systematics of sequence numbers, for example, if the sequence number is not continuous, this would indicate a manipulation.

Subsequent changes within the process information outputted with the protocol signature are thus made detectable by the control system according to the present invention in a reliable manner.

The control system according to the present invention may be combined in an especially simple manner with already existing devices or be integrated into such devices. Thus, only a data interface is needed as a reception module in order to form the control system according to the present invention in addition to a processor for processing data, which may at least partially comprise, for example, the processing module.

Details of the use of such a secret system code for generating a signature are known to the person skilled in the art through many corresponding applications in the area of information technology.

The internal memory may be a memory within the processing module or a separate memory of the control system. The components of the control system may be arranged separately in space from one another or at least partially within a common housing. In particular, the control system may be a part of the device whose process becomes controllable by the control system. The two modules of the control system are separated from one another at least at the software level. The reception module and the processing module are preferably connected to one another in a wired manner. As an alternative, the reception module may be connected to the processing module in a wireless manner.

In the sense of the present invention, the control system is a system that performs a further processing of the outputted process information on the process carried out with the corresponding visible protocol signature and outputs it so reliably that a later control of the process carried out is reliably possible on the basis of this combination of process information and protocol signature, especially that it is possible in such a manner that a manipulation can be detected.

The visible protocol signature is in the sense of the present invention a sequence of characters that can be generated with the use of the sequence number, the process information, the time information and the secret system code in a reproducible manner.

The secret system code is in the sense of the present invention a sequence of characters, which can be used to generate the visible protocol signature electronically.

The sequence number is preferably a continuous sequence number. As a result, it shows a chronological sequence of the carried out process steps of the process.

The reception module is according to the present invention a module for receiving the process information. The signal forwarded from the reception module to the processing module is configured such that the processing module can read at least the corresponding process information from this forwarded signal.

The information received by the reception module may also comprise, in addition to the process information outputted by the processing unit, additional information, which was removed from this originally received information, for example, within the framework of the further processing by the reception module and/or by the processing module, so that the finally outputted process information is the part of the originally received information that is essential for the storage together with the visible protocol signature in the sense of the present invention.

The control system according to the present invention being described here is especially advantageous for medical devices because it shall always be checked in the case of a device error whether the device error has developed systematically due to the device, so that the error must be eliminated for the future application of the device, or whether a user error is present. It is important for such a checking that the stored process information on the operation of the medical device is reliable and cannot be manipulated. As a result, the problem, which has led to the device error, can be eliminated reliably and permanently on the device side or otherwise.

Preferred embodiments of the control system according to the present invention will be described below.

In an especially preferred embodiment, the control system does not have an interface, via which the secret system code can be read. It is ensured in this embodiment in an especially reliable manner that the secret system code is not visible either for the manufacturer of the control system or for the user of the control system. As a result, any subsequent change in the process information by a third device or by a person is noticeable via the visible protocol signature. An unnoticed manipulation can be reliably ruled out. In particular, it can be ensured by avoiding such an interface or by permanently switching off an earlier operability of such an interface that no one, especially no foreign software, has access to the secret system code.

In another advantageous embodiment, the control system has, furthermore, a memory module, which is configured to store the process information with the assigned visible protocol signature. The memory module is preferably arranged in a common housing with at least one of the two other modules of the control system. As an alternative, the memory module is arranged separately from the other components of the control system. The memory module is preferably arranged separately from the internal memory. It is ensured hereby that an access to the memory module for reading the process information and the assigned visible protocol signature does not lead to an access to the secret system code. The memory module preferably has a user interface, which makes it possible for a user of the control system to comprehend the course of the process steps of the process, which were carried out, on the basis of the stored process information. The user can thus read the respective data pairs comprising process information and visible protocol signature via the user interface. The memory module is arranged in an advantageous example detachably in a housing of the control system and/or of the device, especially in a replaceable manner, for example, in the form of an SD card or of another such storage medium.

In another preferred embodiment, the processing module is further configured to assign the time information to the received process information. It is ensured in this embodiment in an especially reliable manner that the time information is assigned to each process information in the same manner, even if corresponding process steps are possibly carried out by different modules and/or are controlled by different processors. This assignment is preferably carried out essentially simultaneously with the assignment of the sequence number, so that a sequence of the sequence numbers essentially corresponds to a chronological sequence of the assigned time of the process information, which time is indicated via the time information. In an alternative or additional embodiment, the reception module is further configured to assign the time information to the received process information. As a result, the time information is assigned directly at the time of receipt of the process information.

The time information especially preferably indicates a time of the process step being currently carried out. The time information may be, for example, a time, an index advancing with time, a time-dependent time signature or the like.

The processing is carried out by the processing module essentially in real time in an especially preferred embodiment. The processing by the control system takes place preferably essentially in real time. It is ensured hereby that the process steps carried out are detected in real time such that a later manipulation with the process information can be detected according to the present invention via the assigned visible protocol signature. Real time preferably means here that the time delay between the receipt of the process information by the reception module and the outputting of process information and of assigned visible protocol signature is shorter than 10 sec, especially shorter than 5 sec, and preferably shorter than 2 sec.

The processing module is especially preferably configured, furthermore, to generate a visible protocol signature for each received process information and to output the process information with the assigned visible protocol signature. It is ensured in this embodiment that an assigned visible protocol signature, which is outputted together with the process information in question, exists for each process information, especially for each carried out process step of the device. As a result, it is possible to detect especially precisely in retrospect how the process is carried out by the device. This makes possible a control of the process carried out in especially small steps.

The visible protocol signature is preferably a so-called Keyed-Hash Message Authentication Code (HMAC). The construction of the HMAC is based, as is known, on a cryptographic hash function and on a secret code, according to the present invention on the secret system code. The exact structure and the usual use of such an HMAC are known, so that they will not be discussed in detail below.

In an advantageous embodiment, the control system has, furthermore, a user interface, which is configured to receive a test user input, the test user input indicating at least a test sequence number, test process information and test time information. The processing module is further configured to generate a comparison protocol signature on the basis of the test user input and the secret system code of the control system. The test user input is preferably forwarded from the user interface to the processing module. Such a forwarding may take place immediately via a communication connection or indirectly via the reception module. The control system makes it advantageously possible in this embodiment to generate the comparison protocol signature for predefined test data. Such a test assignment between test process information and comparison protocol signature makes it possible to check the visible protocol signature that would have to be generated for concrete process information with a corresponding sequence number and time information. A user does not advantageously need to know the secret system code or have it outputted for him for this checking. The user interface may advantageously make possible a wireless communication with an external user device, via which the test user input can, for example, be inputted. Such an external user device may be, for example, a computer, a smartphone, a tablet or the like.

In an especially preferred variant of the above embodiment, the user interface is further configured to receive via the test user input a test protocol signature, and the control system is configured here to compare the test protocol signature with the comparison protocol signature generated on the basis of the test user input and to trigger, based on this comparison, an output that indicates whether the test protocol signature has been generated by the processing module of the device. It can be automatically detected in this variant whether the test protocol signature was generated by the processing module with the secret system code for the rest of the test user input. A subsequent manipulation of these data can be detected hereby. A manipulation is only possible according to the present invention if the secret system code is known. This is avoided by storing the secret system code in the internal memory, to which no external access is preferably possible. The present embodiment with the variant described makes the process control for the process carried out in the device advantageously possible against this background for the process carried out in the device. All the process information that was collected in a predefined time interval of the process can preferably be checked in an automated manner with respect to its visible protocol signature. A manipulation of stored process information, such as, e.g., log entries, can be successfully detected hereby by the control system itself.

In another advantageous variant, the control system is configured to check in an automated manner a past time interval, e.g., a predefined time interval or a randomly selected time interval, to determine whether the process information stored during this time interval leads the assigned visible protocol signature together with the secret system code. As a result, the control system can check itself in an automated manner in order to detect whether a manipulation with the outputted data has taken place. The processing module has at least partial access in this variant to the outputted process information and to the respective assigned visible protocol signature as well as to the corresponding sequence number and to the corresponding time information.

In another embodiment, the control system has a testing device, which is configured to receive at least one piece of process information with the assigned visible protocol signature from the processing module and to determine on the basis of a stored public system code whether the visible protocol signature has been generated by the processing module for the process information. The secret system code is part in this embodiment of an asymmetric encryption to generate the protocol signature.

The process carried out now is asymmetric in the respect that only the processing module is capable of determining the visible protocol signature, because only the processing module has access to the secret system code. The conversion of the protocol signature back into the information being stored therein concerning the process carried out, such as at least parts of the process information, of the sequence number and of the time information, can, however, be carried out by anyone with the use of the stored public system code. Thus, anyone can check whether the visible protocol signature fits the correspondingly assigned process information, without the secret system code having to be known for this. This makes it advantageously possible to check the outputted data by the testing device in a simple manner. In particular, a manipulation with the outputted data can be detected thereby in a short time. The testing device is preferably configured to communicate with the processing module in a wireless manner and to access the stored public system code. As a result, no physical presence is advantageously necessary in the vicinity of the processing module in order to detect a manipulation with the outputted data.

According to a second aspect of the present invention, a medical device with a control system according to at least one of the above embodiments is proposed to accomplish the above-mentioned object.

Such a medical device has all the advantages of the control system. Further, the arrangement of the control system within the medical device makes possible a rapid, reliable data exchange between the corresponding components of the control system.

In one embodiment, the testing device of the control system forms a separate part of the medical device, which part may be arranged separated in space from the medical device.

The corresponding process information is preferably sent for each process step of a process carried out by the medical device to the reception module. As a result, all process steps of the medical device can be detected reliably and protected with the respective visible protocol signature from manipulations by the assignment according to the present invention such that a manipulation can at least be reliably detected.

According to a third aspect of the present invention, a process is proposed for making possible a process control for a process carried out on a device in order to accomplish the above-mentioned object. The process according to the present invention comprises the following steps:

provision, especially storage, of a secret system code exclusively in an internal memory of a control system provided for carrying out the process;

receipt of process information, wherein the process information pertains to currently performed process steps of the process;

assignment of a sequence number to the process information;

generation of a visible protocol signature on the basis of the sequence number, of the process information, of time information and of the secret system code;

assignment of the visible protocol signature to the process information; and outputting of the process information with the assigned visible protocol signature.

The process according to the third aspect of the present invention is carried out according to the present invention by a control system according to the first aspect of the present invention. The process thus has the same advantages as the control system according to the present invention.

The provision of the secret system code for carrying out the process comprises according to the present invention the provision of the secret system code for generating the visible protocol signature.

The first step of the process according to the present invention is preferably carried out such that not even the manufacturer of the corresponding device and/or of the corresponding control system knows the secret system code. This can be embodied, for example, such that a predefined property of the system, which is not predictable for the manufacturer, is used to set the secret system code. This may be, for example, a predefined number of digits of a random number determined once. Algorithms for determining such a random number are generally known and will not be explained in detail below. Furthermore, a predefined number of decimal places of a time of a predefined event may be used as a secret system code, e.g., the time of the first-time start of the processing module. Further comparable sources of secret system codes unforeseeable for the manufacturer are known will not therefore be explained in detail below.

In a preferred embodiment, the process according to the present invention has, furthermore, the following steps:
  receipt of a test user input, wherein the test user input indicates at least one test sequence number, test process information and test time information;
  generation of a comparison protocol signature on the basis of the test user input and of the secret system code of the control system; and
  comparison of the comparison protocol signature with a known test protocol signature to determine whether the known test protocol signature was generated by the control system provided for carrying out the process.

It is advantageously ensured in this embodiment that a concrete data set of sequence number, process information, time information and protocol signature can be checked to determine whether the protocol signature was generated with the secret system code. A subsequent manipulation with the data, after the visible protocol signature has been generated, can thus be reliably detected.

According to a fourth aspect of the present invention, a computer program with a program code is proposed for carrying out a process according to an embodiment of the third aspect of the present invention to accomplish the above-mentioned object when the program code is executed on a computer, on a processor or on a programmable hardware component. A plurality of steps of the process according to the present invention are preferably carried out by a common computer, by a common processor or by a common programmable hardware component. The individual steps are preferably separated from one another here at least at the software level by corresponding software blocks. All steps of the process according to the present invention are especially preferably carried out on a common computer, on a common processor or on a common programmable hardware component.

The present invention shall now be explained in more detail on the basis of advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
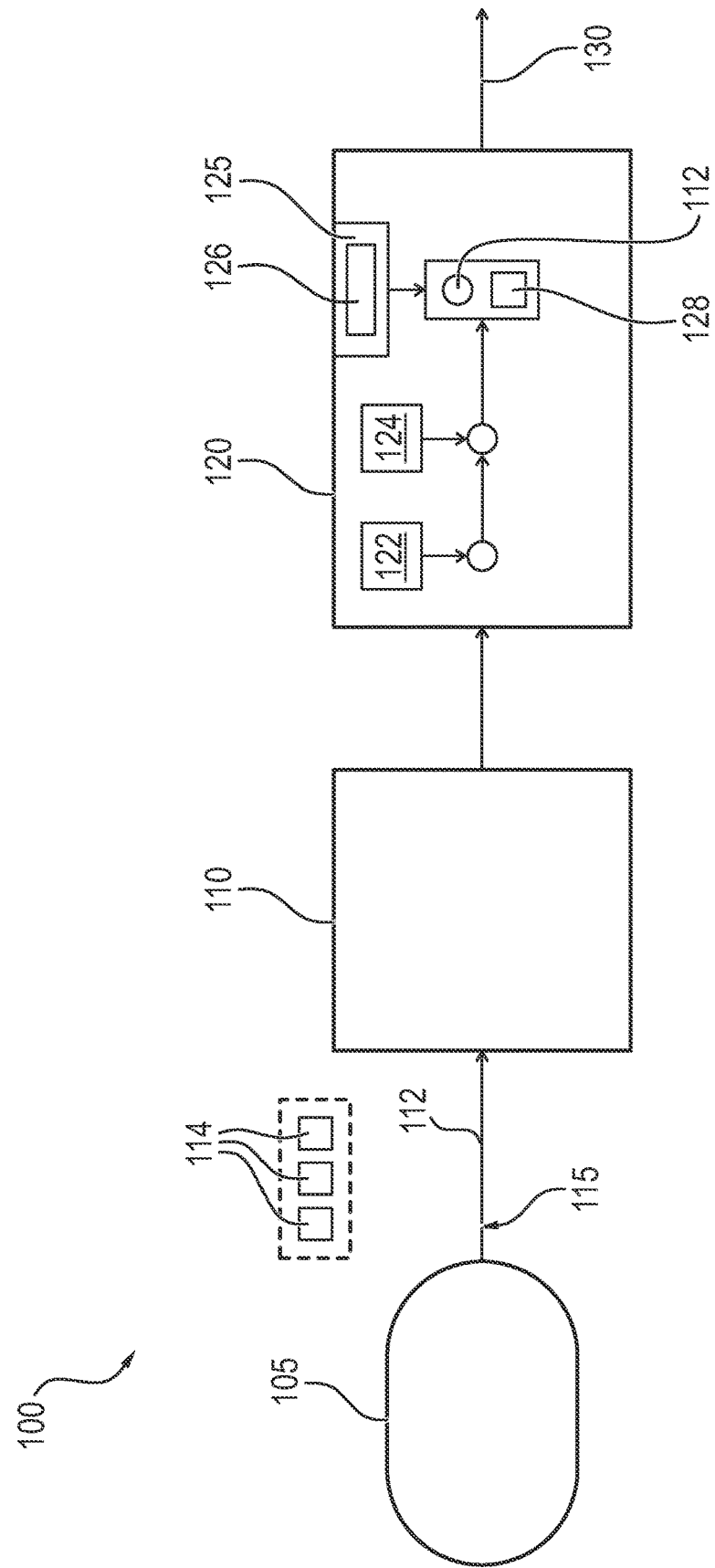
FIG. 1 is a schematic view of a first exemplary embodiment of a control system according to a first aspect of the present invention.

Referring to the drawings, FIG. 1 shows a schematic view of a first exemplary embodiment of a control system 100 according to a first aspect of the present invention.

The control system 100 for a device 105 is configured to make possible a process control for a process carried out on the device 105. The control system 100 has a reception module 110 and a processing module 120 for this.

The reception module 110 is configured to receive process information 112, wherein the process information 112 pertains to currently carried out process steps 114 of the process. The receipt may take place in a wireless or wired manner. The device 105 is connected directly to the reception module 110 via a device cable 115 in the example shown. The device 105 is an external device in this case, which does not comprise the control system 100.

The processing module 120 is configured to assign a sequence number 122 to the received process information. The sequence number 122 is a continuous number, which indicates a sequence of the process steps 114 carried out by the device 105. Furthermore, the processing module 120 is configured to assign time information 124 to the received process information, wherein the time information indicates a time of the process step 114 currently being carried out. Finally, the processing module 120 comprises an internal memory 125, in which a secret system code 126 is stored. In one exemplary embodiment, not shown, the internal memory of the control system is arranged outside the processing module. Finally, the processing module 120 is configured according to the present invention to generate a visible protocol signature 128 on the basis of the sequence number 122, of the process information 112, of the time information 124 and of the secret system code 126 of the control system 100 and to assign it to the process information 120. The visible protocol signature 128 is a sequence of characters, which are stored together with the process information 112. The process information 112 with the assigned visible protocol signature 128 is outputted for this purpose by the processing module 120 within the framework of an output 130.

The output 130 is carried out in the exemplary embodiment shown in a wired or wireless manner to a data bank, not shown, outside the control system 100. As an alternative or in addition, a memory module, in which the process information with the assigned visible protocol signature is stored, may be provided within the control system.

The process information 112 is shown in FIG. 1 both as received process information of the reception module 110 and as assigned process information within the processing module 120. The process information 112 is the same here in the exemplary embodiment shown, and a further processing of the contents of the reception module 110 is not carried out. In an alternative or additional exemplary embodiment, the assigned process information within the processing module is processed process information of the originally received process information and it therefore differs in terms of contents from this. For example, data can thus be compressed during the processing of the process information, as a result of which the processed process information is not identical in terms of content to the received process information. For reasons of clarity, the process information is designated by 112 in all exemplary embodiments. This designation thus always comprises the part of the process information that is still contained in the processed process information.

The control system 100 especially preferably does not have an interface, via which the secret system code 126 can be read. It is ensured hereby that the secret system code 126 remains secret. The secret system code 126 is generated in the exemplary embodiment shown by means of a random number generator and is stored directly in the internal memory 125. It is ensured hereby that neither the manufacturer nor the user of the control system 100 knows the secret system code 126. As a result, manipulation of the stored data is made detectable according to the present invention. Should something be changed in the data, the secret system code 128 will no longer fit the changed process information, the changed sequence number and/or the changed time information.

The processing of the data by the processing module 120 takes place in the exemplary embodiment essentially in real time. This means that a time delay between the receipt of the process information and the output of process information and assigned visible protocol signature preferably equals less than 10 sec, especially less than 5 sec, and especially preferably less than 2 sec. The corresponding process information 112 is received and processed here for each process step 114 of the process carried out by the device 105, so that the visible protocol signature 128 is assigned to the corresponding process information 112.

The reception module 110 and the processing module 120 are controlled by a single processor, not shown, in the exemplary embodiment shown. The data transmission between these two modules 110, 120 of the control system 100 takes place in the exemplary embodiment shown within the processor at the software level. In an alternative exemplary embodiment, not shown, the processing module and the reception module are connected to one another in a wireless manner.

The visible protocol signature 128 in the exemplary embodiment shown is a so-called Keyed-Hash Message Authentication Code (HMAC), which is known to be based from on a so-called Hash function and a secret code. The secret code is the secret system code 126 in this case. The exact construction of such an HMAC is generally known and will not therefore be explained in detail below.

The processed process information 112 is represented by log entries of the device 105, which shall make it possible to reconstruct the process steps carried out by the device 105 for a later checking. A later change of these log entries can be reliably detected according to the present invention after the assignment of the visible protocol signature 128 with the visible protocol signature 128 due to the assignment.

The described process with the use of a single secret system code 126 corresponds in the exemplary embodiment shown to a symmetrical encryption, because the secret system code 126 must always be used even for checking data in order to check for the presence of a manipulation. An exemplary construction for checking data in case of the use of a symmetrical encryption is described within the framework of FIG. 3. An alternative and/or additional construction for checking data in case of the use of an asymmetric encryption is described within the framework of FIG. 4.

The control system may be fully or partially integrated into the device or, as is shown in FIG. 1, it may be completely separated from the device. Parts of the control system or the entire control system may be in a separate housing.

Figure 2:
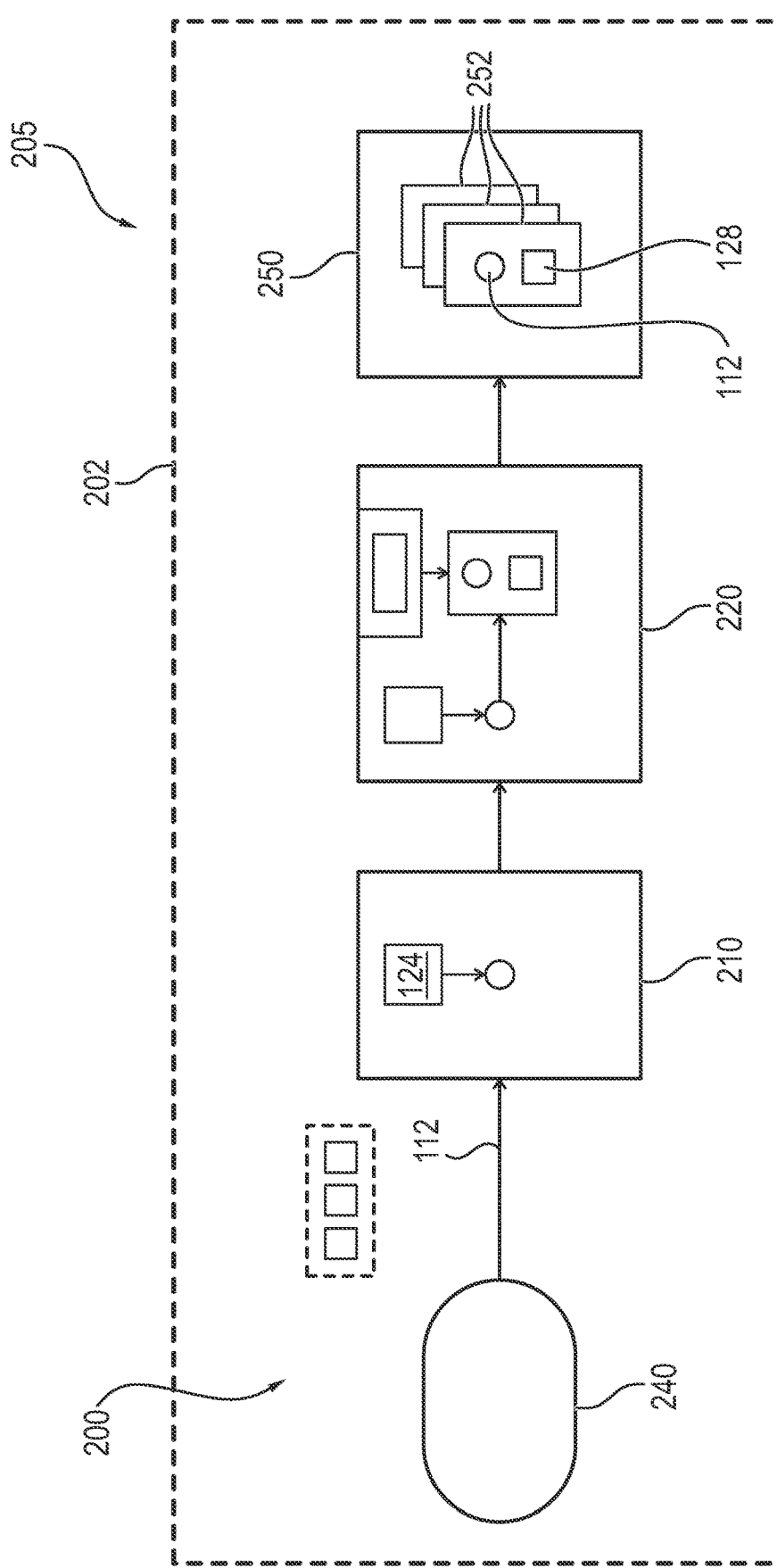
FIG. 2 is a schematic view of a second exemplary embodiment of a control system according to the first aspect of the present invention.

FIG. 2 shows a schematic view of a second exemplary embodiment of a control system 200 according to the first aspect of the present invention.

The control system 200 differs from the control system 100 shown in FIG. 1 in that the housing 202 of the device 205 encloses the control system 200. The process information 112 is outputted by a corresponding control unit 240 of the device 205 to the reception module 210. The control system 200 is not consequently a separate control system in this exemplary embodiment, but an integral part of the device 205. The device 205 is a medical device in this case. Against this background, the control system 200 according to the present invention makes possible a reliable storage of treatment data, where any possible manipulations can always be detected.

Furthermore, the reception module 210 is configured to assign the time information 124 to the process information 112. This assignment does not therefore take place as in the control system 100 within the processing unit 220.

Finally, the control system 200 differs from the control system 100 in that it has, furthermore, a memory module 250, which is configured to store the process information 112, preferably the process information processed by the reception module 210 and/or by the processing module 220, with the assigned visible protocol signature 128. A sequence of process information 112 with the assigned visible protocol signature 128 is thus stored in the memory module 250 as a sequence of data pairs 252, which correspond to the executed sequence of process steps of the device 250.

The memory module 250 is connected to the processing module 220 in a wired manner. In one exemplary embodiment, not shown, the memory module can be removed from the device and from the corresponding control system and/or replaced, as a result of which the stored data, for example, the data of a hospital, can be stored at a central location. For example, regional requirements imposed on data protection can be complied with. The memory module is, for example, a portable storage medium, such as a DVD, a CD, an SD card, a disk, a USB stick or the like.

In one exemplary embodiment, not shown, the memory module is an external memory module, which is not a part of the control system.

Figure 3:
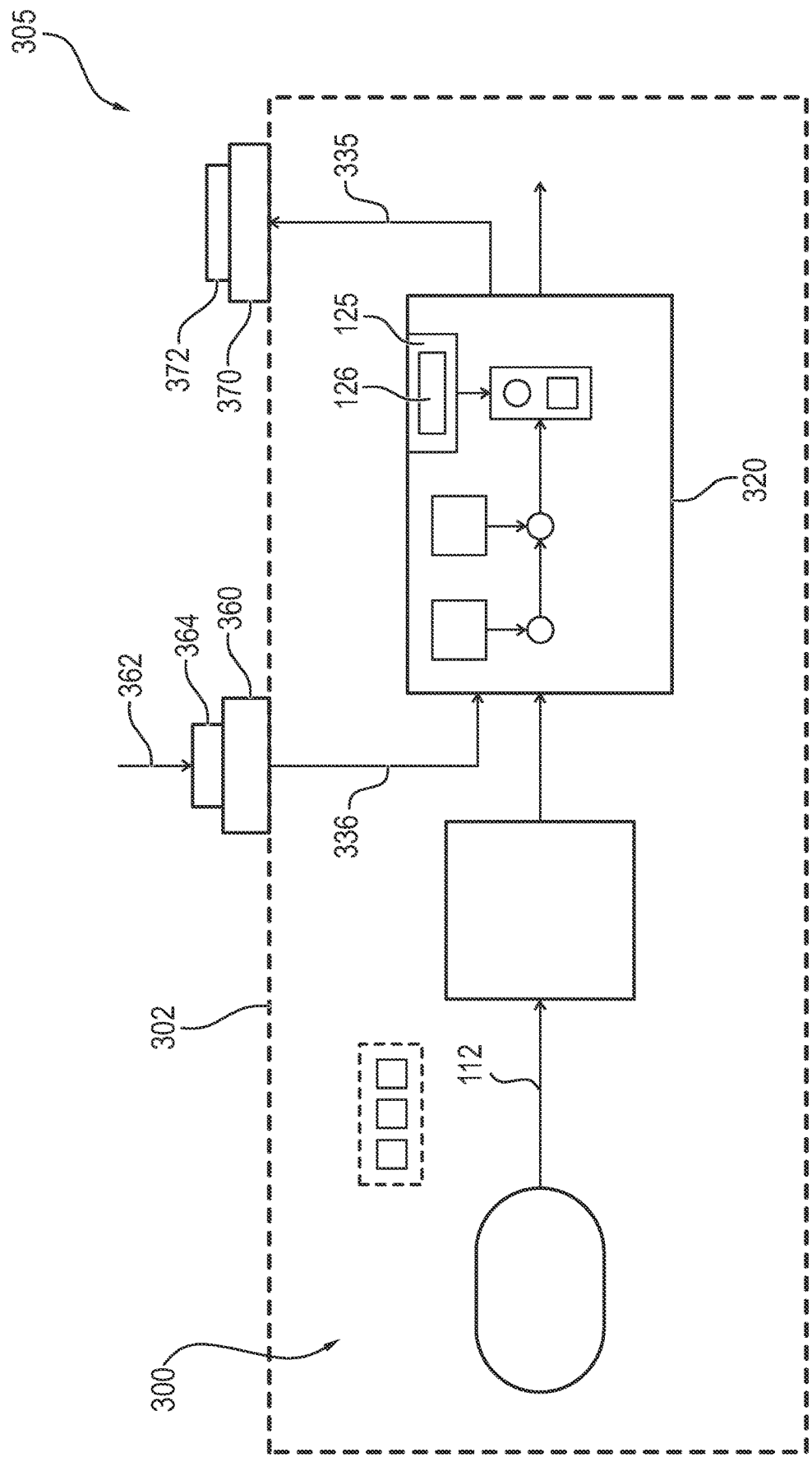
FIG. 3 is a schematic view of a third exemplary embodiment of a control system according to the first aspect of the present invention.

FIG. 3 shows a schematic view of a third exemplary embodiment of a control system 300 according to the first aspect of the present invention.

The control system 300 differs from the control system 100 shown in FIG. 1 in that the device 305 with its housing 302 surrounds again the control system 300, so that the control system 300 is an integral part of the device 305. In addition, a user interface 360 of the control system 300, which is configured to receive a test user input 362 via an input device 364, in this case a keyboard, a touch display, a data reader or the like, and to forward it to the processing module 320, is provided at the device 305. This forwarding takes place in the exemplary embodiment shown directly in a wired manner via an interface connection 366. In one exemplary embodiment, not shown, the user interface is connected to the reception module and is connected via the reception module indirectly to the processing unit.

The test user input 362 indicates in this case a test sequence number, test process information and test time information. In addition, a test protocol signature is received here via the test user input 362.

These received test data are used by the processing module 320 to generate a comparison protocol signature, just as in the case of the process information 112 received outside this test operation, with the use of the secret system code 126. This comparison protocol signature is the protocol signature that would have been generated by the processing module 320 if the test process information had been processed as process information 112 at the time indicated by the test time information with the sequence number corresponding to the test sequence number. The generated comparison protocol signature can now be compared with the test protocol signature. It becomes clear as a result whether the test protocol signature is the visible protocol signature that would have been generated by the processing module 320 for the additional test data outside the test operation.

A corresponding test output 335 takes place via an output module 370, which has a display 372 for visualizing the output in the exemplary embodiment shown. The output module 370 is arranged at the housing 302 of the device 305. The test output 335 indicates here the result of the comparison between the comparison protocol signature and the test protocol signature. As a result, it is indicated via the test output 335 whether the test protocol signature has been generated by the processing module 320 of the device 305.

A checking of earlier data, i.e., a checking whether stored process information and the assigned visible protocol signature have been manipulated or not, is possible in the exemplary embodiment shown only directly at the device 305 with the control system 300, because the secret system code 126 is necessary for this checking and this is stored in the internal memory 125 only. An exemplary embodiment, which is an alternative or additional embodiment to this, with a checking device, especially with a mobile checking device, is shown in FIG. 4.

Figure 4:
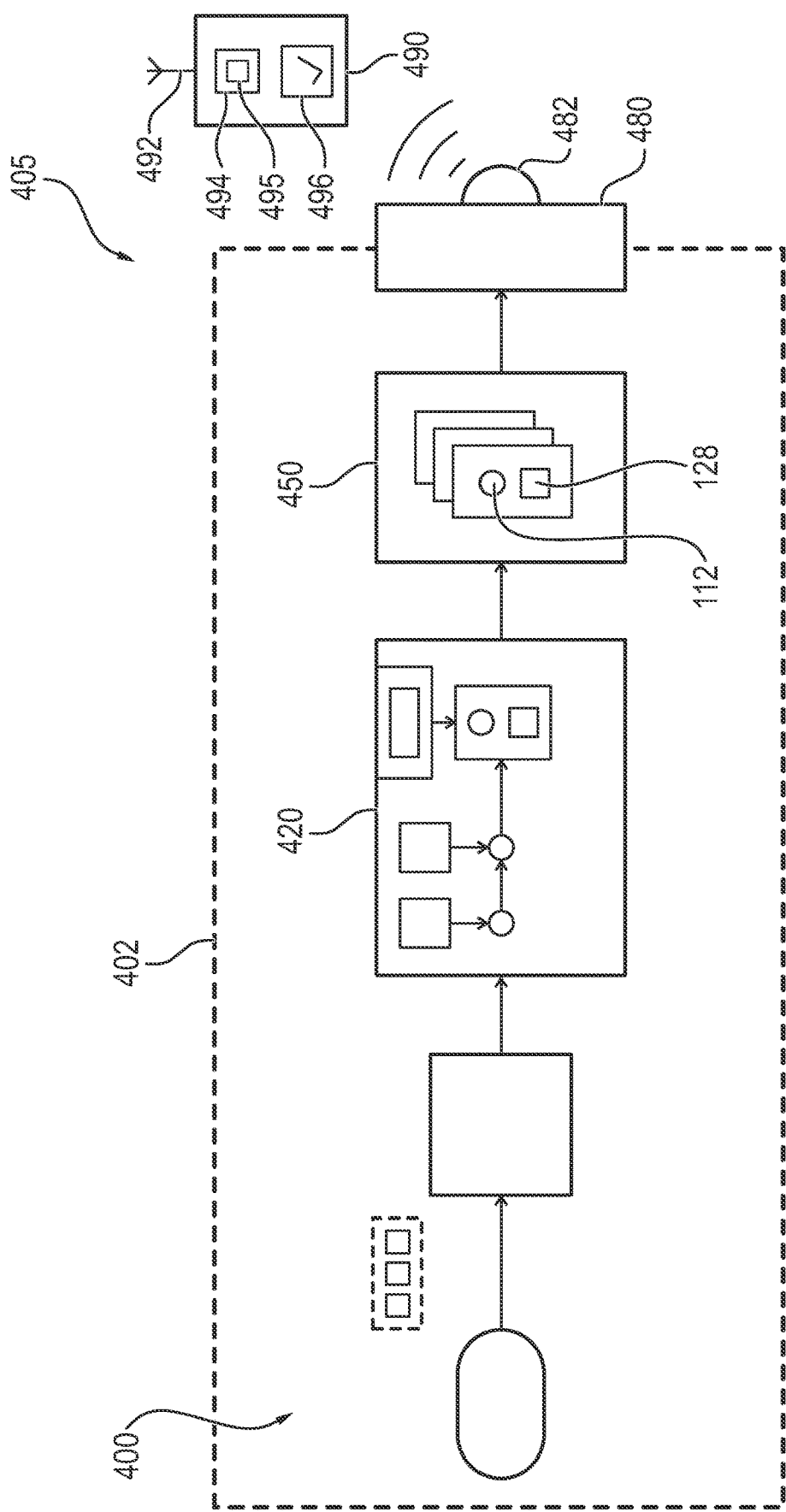
FIG. 4 is a schematic view of a fourth exemplary embodiment of a control system according to the first aspect of the present invention.

FIG. 4 shows a schematic view of a fourth exemplary embodiment of a control system 400 according to the first aspect of the present invention.

The control system 400 differs from the control system 300 shown in FIG. 3 in that it does not have a user interface and an output module for communication with a user, but it can communicate with a user via a sending module 480 with a wireless interface 482, and it can communicate especially in a wireless manner. The control system additionally comprises for this purpose a checking device 490 arranged outside the housing 402 of the device 405, especially a mobile checking device, which can communicate with the wireless interface 482 via an antenna module 492.

In addition to the antenna module 492, the checking device 490 has a local checking memory 494, in which at least one stored public system code 495 is contained, which is assigned to the processing module 420 of the control system 400. A plurality of public system codes 495, which are assigned each to a processing module of a control system according to the present invention, are stored in the local checking memory 494 in the exemplary embodiment shown. Furthermore, the checking device 490 has a display, which is a touch display 496 in this case. A user of the checking device 490 selects via the touch display 496 at least one combination of process information 112 and assigned visible protocol signature 128, which combination is stored in the memory module 450 of the control system 400, in order to determine on the basis of the stored public system code 495 whether the selected visible protocol signature 128 has been generated by the processing module 420 for the selected process information 112.

A visible protocol signature for process information cannot be determined via the stored public system code 495, because this could make a manipulation of process information possible. The public system code 495 only allows a decryption of the visible protocol signature 128 and as a result a comparison between the data stored in the visible protocol signature 128 and the actually assigned process information in this exemplary embodiment. As a result, it can be determined by means of the checking device 490 whether process information or the assigned visible protocol signature has been manipulated within the memory module. This checking is advantageously carried out via a mobile device, because no physical presence of the people performing the checking is necessary as a result in the immediate environment of the device 405. The wireless interface 482 may be configured for the wireless communication with the checking device 490 via a WLAN connection, a ZigBee connection, a Bluetooth connection, a BLE connection or the like.

Figure 5:
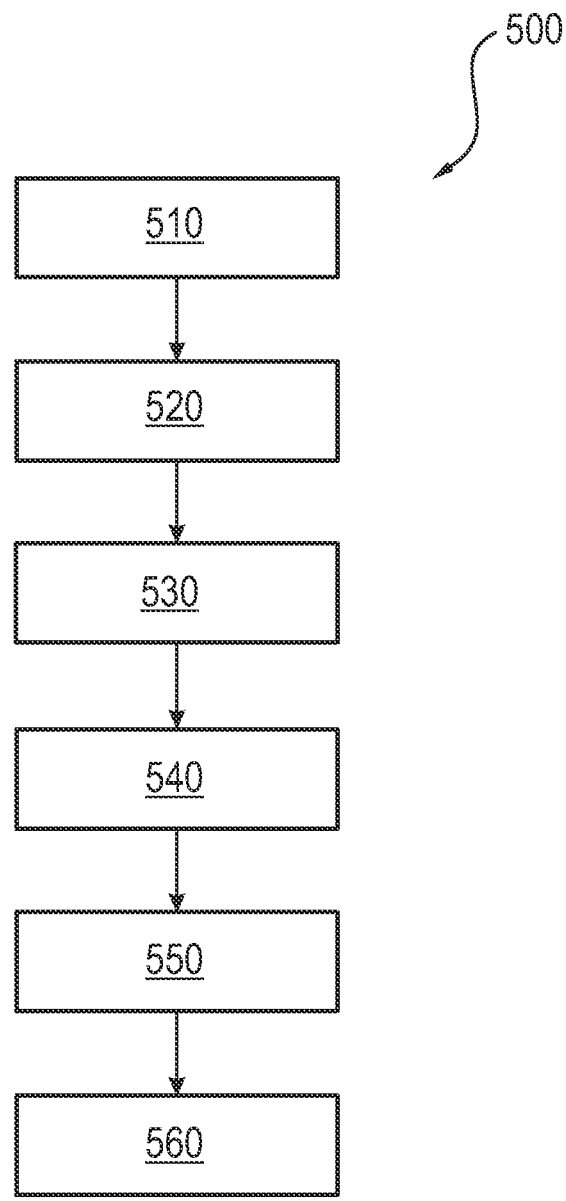
FIG. 5 is a flow chart of an exemplary embodiment of a process according to a third aspect of the present invention.

FIG. 5 shows a flow chart of an exemplary embodiment of a process 500 according to a third aspect of the present invention.

The process 500 according to the present invention is configured to make possible a process control for a process carried out on a device. It has for this purpose the steps described below.

A first step 510 comprises the provision, especially storage, of a secret system code exclusively in an internal memory of a control system provided for carrying out the process.

A next step 520 comprises the receipt of process information, wherein the process information pertains to process steps of the process that are currently being carried out.

A next step 530 comprises an assignment of a sequence number to the process information.

Another step 540 comprises the generation of a visible protocol signature on the basis of the sequence number, the process information, time information and the secret system code.

A next step 550 comprises the assignment of the visible protocol signature to the process information.

A final step 560 comprises the outputting of the process information with the assigned visible protocol signature.

The first process step 510 is carried out according to the present invention a single time only. This step is carried out such that neither the manufacturer of the corresponding device nor the user of this device can know the secret system code. Such a code may be generated, for example, by generating a random number or by an especially precise analysis of a system and/or device property. For example, a predefined number of decimal places of an installed resistance value, a system time in case of a single-time event, for example, a first-time start of the system or the like may thus be used to generate and to store the secret system code according to the present invention.

Steps 520, 530, 540 and 550 are preferably carried out consecutively essentially in real time, so that these steps are carried out in less than 10 sec, especially in less than 5 sec, and preferably in less than 2 sec. The output within the framework of step 560 likewise takes place preferably essentially in real time. As an alternative or in addition, this output takes place such that process information and assigned protocol signature are outputted together for all process information that was collected within a predefined time interval.

A first step of the process according to the present invention preferably comprises the generation of the secret system code. The generation and the storage of the system code take place preferably nearly simultaneously.

Time information, e.g., a time or another time-dependent information, which is suitable for use as time information for the process information, especially as a time stamp for the process information, is preferably also assigned to the process information immediately before or after step 530, i.e., before or after the assignment of the sequence number.

In one exemplary embodiment of the process, the secret system code is generated such that even though reading of the system code is possible, this has not verifiably happened. This may be achieved, for example, by generating a random number externally and by passing this random number subsequently over into the processing module.

In an especially preferred exemplary embodiment of the process according to the present invention, this process comprises the following steps:

receipt of a test user input, wherein the test user input indicates at least a test sequence number, test process information and test time information;

generation of a comparison protocol signature on the basis of the test user input and the secret system code of the control system; and comparison of the comparison protocol signature with a known test protocol signature to determine whether the known test protocol signature was generated by the control system provided for carrying out the process.

It is ensured in this exemplary embodiment that it is possible to check on the basis of the test user input whether a manipulation with process information has taken place. If a manipulation has occurred, the assigned visible protocol signature would not fit the process information, because the fitting protocol signature can only be determined with the use of the secret system code. This secret system code is stored, however, such that no direct access is possible to it.

While specific embodiments of the invention have been shown and described in detail to illustrate the application of the principles of the invention, it will be understood that the invention may be embodied otherwise without departing from such principles.

LIST OF REFERENCE NUMBERS

100, 200, 300, 400 Control system
202, 302, 402 Housing
105, 205, 305, 405 Device
110, 210 Reception module
112 Process information
114 Process step
115 Device cable
120, 220, 320, 420 Processing module
122 Sequence number
124 Time information
125 Internal memory
126 Secret system code
128 Visible protocol signature
130 Output
240 Control unit of the device
250, 450 Memory module
252 Data pairs
335 Test output
360 User interface
363 Test user input
364 Input device
370 Output module
372 Display
480 Sending module
482 Wireless interface
490 Checking device
492 Antenna module
494 Local checking memory
495 Public system code
496 Touch display
500 Process
510, 520, 530, 540, 550, Process steps
560

What is claimed is:

1. A control system for a device with a process control for a device process carried out on the device, the control system comprising:
    an internal memory;
    a reception module configured to receive process information, wherein the process information pertains to device process steps of the device process currently being carried out; and
    a processing module configured to assign a sequence number to the received process information and to generate a visible protocol signature based on the sequence number, the process information, time information and a secret system code of the control system and to assign the visible protocol signature to the process information and to output the process information with the assigned visible protocol signature, wherein the secret system code is stored exclusively in the internal memory.

2. A control system in accordance with claim 1, wherein the control system does not have an interface, via which the secret system code can be read.

3. A control system in accordance with claim 1, further comprising a memory module configured to store the process information with the assigned visible protocol signature.

4. A control system in accordance with claim 1, wherein the processing module is further configured to assign the time information to the received process information.

5. A control system in accordance with claim 1, wherein the time information indicates a time of the process currently being carried out.

6. A control system in accordance with claim 1, wherein the processing is carried out by the processing module in real time.

7. A control system in accordance with claim 1, wherein the processing module is configured to generate a visible protocol signature for each received process information and to output the process information with the assigned visible protocol signature.

8. A control system in accordance with claim 1, further comprising a user interface configured to receive a test user input and to forward the test user input to the processing module, wherein:
    the test user input indicates at least a test sequence number, test process information and test time information; and
    the processing module is configured to generate a comparison protocol signature based on the test user input and the secret system code of the control system.

9. A control system in accordance with claim 8, wherein:
    the user interface is further configured to receive a test protocol signature via the test user input; and the control system is configured to compare the test protocol signature with the comparison protocol signature generated based on the test user input and to trigger, based on the comparison, a test output, which indicates whether the test protocol signature has been generated by the processing module.

10. A control system in accordance with claim 1, further comprising a checking device configured to receive at least one piece of process information with the assigned visible protocol signature from the processing module or from the memory module and to determine based on a stored public system code, which is assigned to the processing module, whether the visible protocol signature has been generated by the processing module for the process information.

11. A medical device comprising a control system for a process control for a medical device process carried out on the medical device, the control system comprising:
   an internal memory;
   a reception module configured to receive process information, wherein the process information pertains to medical process steps of the medical device process currently being carried out by the medical device; and
   a processing module configured to assign a sequence number to the received process information and to generate a visible protocol signature based on the sequence number, the process information, time information and a secret system code of the control system and to assign the visible protocol signature to the process information and to output the process information with the assigned visible protocol signature, wherein the secret system code is stored exclusively in the internal memory.

12. A medical device in accordance with claim 11, wherein the corresponding process information is sent to the reception module for each process step of a process carried out by the medical device.

13. A medical device in accordance with at least claim 11, wherein the processing module is further configured to assign the time information to the received process information and the time information indicates a time of the process currently being carried out by the medical device.

14. A medical device in accordance with at least claim 11, wherein the processing module is configured to generate a visible protocol signature for each received process information and to output the process information with the assigned visible protocol signature.

15. A medical device in accordance with at least claim 11, wherein:
   the control system further comprises a user interface configured to receive a test user input and to forward the test user input to the processing module;
   the test user input indicates at least a test sequence number, test process information and test time information; and
   the processing module is configured to generate a comparison protocol signature based on the test user input and the secret system code of the control system.

16. A medical device in accordance with claim 15, wherein:
   the user interface is further configured to receive a test protocol signature via the test user input; and
   the control system is configured to compare the test protocol signature with the comparison protocol signature generated based on the test user input and to trigger, based on the comparison, a test output, which indicates whether the test protocol signature has been generated by the processing module.

17. A medical device in accordance with claim 11, wherein the control system further comprises a checking device configured to receive at least one piece of process information with the assigned visible protocol signature from the processing module or from the memory module and to determine based on a stored public system code, which is assigned to the processing module, whether the visible protocol signature has been generated by the processing module for the process information.

18. A process for process control for a device process carried out on a device, the process comprising the steps of:
   providing a secret system code exclusively in an internal memory of a control system provided for carrying out the device process;
   receiving process information, wherein the process information pertains to currently carried out process steps of the device process;
   assigning a sequence number to the process information;
   generating a visible protocol signature based on the sequence number, of the process information, of time information and of the secret system code;
   assigning the visible protocol signature to the process information; and
   outputting the process information with the assigned visible protocol signature.

19. A process in accordance with claim 18, further comprising the steps of:
   receiving a test user input, wherein the test user input indicates at least a test sequence number, test process information and test time information;
   generating a comparison protocol signature based on the test user input and the secret system code of the control system; and
   comparing the comparison protocol signature with a known test protocol signature to determine whether the known test protocol signature was generated by the control system provided for carrying out the device process.

20. A process in accordance with claim 18, wherein a computer program, with a program code, carries out a at least some steps of the process when the program code being executed on a computer, on a processor or on a programmable hardware component.

* * * * *